United States Patent [19]

Evans et al.

[11] 4,363,811
[45] Dec. 14, 1982

[54] ANTI-HYPERTENSIVE CHROMANOL DERIVATIVES

[75] Inventors: John M. Evans, Roydon; Graham A. Showell; Charles S. Fake, both of Harlow, all of England

[73] Assignee: Beecham Group Limited, England

[21] Appl. No.: 186,708

[22] Filed: Sep. 12, 1980

[30] Foreign Application Priority Data

Sep. 28, 1979 [GB] United Kingdom ............... 7933683
May 3, 1980 [GB] United Kingdom ............... 8014933

[51] Int. Cl.³ ................ A61K 31/445; C07D 405/04
[52] U.S. Cl. ................................. 424/267; 424/246;
424/248.54; 424/248.55; 424/248.56;
424/248.57; 424/248.58; 424/270; 424/272;
424/274; 424/283; 544/58.7; 544/62; 544/151;
546/196; 548/146; 548/214; 548/215; 548/240;
548/525; 549/399
[58] Field of Search ............ 260/345.3, 345.5, 326.34,
260/326.5 CA; 546/196; 548/146, 214, 215,
240; 544/151, 58.7, 62; 424/267, 274, 270, 272,
283, 248.54, 248.55, 248.56, 248.58, 246, 248.57

[56] References Cited

U.S. PATENT DOCUMENTS 4,048,317  9/1977  Watts ................................. 546/196
4,251,537  2/1981  Evans ............................. 546/196 X

FOREIGN PATENT DOCUMENTS 2713670 10/1977 Fed. Rep. of Germany .

1548221 7/1979 United Kingdom .

Primary Examiner—Richard A. Schwartz
Attorney, Agent, or Firm—Jacobs & Jacobs

[57] ABSTRACT

Compounds of the formula (I):

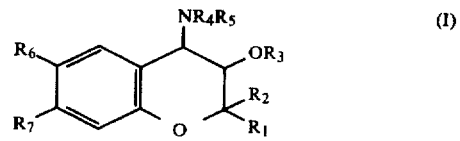

and salts and pro-drugs thereof, wherein:
  $R_1$ is a hydrogen atom or a lower alkyl group;
  $R_2$ is a hydrogen atom or a lower alkyl group;
  $R_3$ is a hydrogen atom or a lower alkyl group;
  $R_4$ is a hydrogen atom or an alkyl group;
  $R_5$ is a lower alkyl or a substituted alkyl group;
  or $R_4$ and $R_5$ are joined so that together with the nitrogen atom to which they are attached they form a 5-, 6- or 7-membered ring optionally containing an oxygen or sulphur atom;
  $R_6$ is an electron donating group;
  $R_7$ is an electron withdrawing group; and
  the $NR_4R_5$ and $OR_3$ moieties are trans having antihypertensive activity, pharmaceutical compositions containing them and processes for their preparation.

9 Claims, No Drawings

ANTI-HYPERTENSIVE CHROMANOL DERIVATIVES

This invention relates to chromanol derivatives, a process for their preparation, and to their use.

U.K. Pat. Nos. 1,495,526 and 1,511,187 disclose that derivatives of trans-3-hydroxy-4-aminochroman have blood pressure lowering activity.

A group of compounds have now been found that also possess good blood pressure lowering activity, with low levels of unwanted cardiac effects.

Accordingly, the present invention provides the compounds of the formula (I):

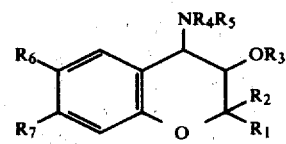

and salts and pro-drugs thereof, wherein:
$R_1$ is a hydrogen atom or a lower alkyl group;
$R_2$ is a hydrogen atom or a lower alkyl group;
$R_3$ is a hydrogen atom or a lower alkyl group;
$R_4$ is a hydrogen atom or an alkyl group;
$R_5$ is a lower alkyl or a substituted alkyl group;
or $R_4$ and $R_5$ are joined so that together with the nitrogen atom to which they are attached they form a 5-, 6- or 7-membered ring optionally containing an oxygen or sulphur atom;
$R_6$ is an electron donating group;
$R_7$ is an electron withdrawing group; and
the $NR_4R_5$ and $OR_3$ moieties are trans.

The terms 'electron withdrawing group' and 'electron donating group' are terms well recognised in the art. Such groups are readily identifiable by the skilled man. Standard references to such terms include Finar, 'Organic Chemistry' Vol. 1, pp 21, 22.

When used herein the term "alkyl" means an alkyl group of up to 5 carbon atoms; the term "lower" means a group of up to 3 carbon atoms; and term "substituted alkyl" means a straight chain alkyl group of at least 3 carbon atoms terminally substituted by a chlorine atom.

Suitably $R_1$ is a hydrogen atom or a methyl or ethyl group. Most suitably $R_1$ is a methyl group.

Suitably $R_2$ is a hydrogen atom or a methyl or ethyl group. Most suitably $R_2$ is a methyl group.

Apt values for $R_3$ include the hydrogen atom and the methyl and ethyl groups. Particularly apt values for $R_3$ include the hydrogen atom and the methyl group. A favoured value for $R_3$ is the hydrogen atom.

Suitable acyclic values for the $NR_4R_5$ moiety include those wherein $R_4$ is a hydrogen atom or methyl group and $R_5$ is an alkyl group. Specific values for acyclic $NR_4R_5$ moieties include dimethylamino, isopropylamino and t-butylamino.

Suitable cyclic values for the $NR_4R_5$ moiety include those of the sub-formula (a):

wherein X is a bond, a methylene group, an ethylene group, an ethylidene group, an oxygen, or a sulphur atom. Most suitably X is a bond or a methylene group.

Suitable electron donating groups $R_6$ include the amino, lower acylamino, lower alkylamino, lower dialkylamino, hydroxyl, lower alkoxyl and lower alkyl groups. Apt groups $R_6$ thus include the $NH_2$, $NH.CO.CH_3$, $OCH_3$, $OH$ and $CH_3$ groups. Favoured groups $R_6$ include the $NH_2$, $NH.CO.CH_3$, $OCH_3$ and $OH$ groups of which the $NH_2$ and $NH.CO.CH_3$ are particularly favoured.

Suitable electron withdrawing groups $R_7$ include the nitro, cyano, carboxamido, acetyl and lower alkoxycarbonyl groups. Favoured groups $R_7$ include the nitro, cyano, carboxamido and acetyl groups. Particularly favoured $R_7$ groups are the nitro and cyano groups.

Suitable pro-drugs of the compounds of the formula (I) include esters of those compounds wherein $R_3$ is a hydrogen atom. Suitable esters include those of fatty acids up to 18 carbon atoms more suitably those of up to 4 carbon atoms. Examples of such esters include those of acetic, propionic, butyric, oleic, palmitic, stearic, benzoic, pivalic and the like acids.

Suitable salts of the compounds of this invention include acid addition salts with pharmaceutically acceptable inorganic or organic acids such as hydrochloric, hydrobromic, phosphoric, sulphuric, toluene sulphonic, methane sulphonic, acetic, propionic, succinic, citric, lactic, tartaric, maleic, mandelic or like acid.

Favoured compounds of this invention include those of the formula (II):

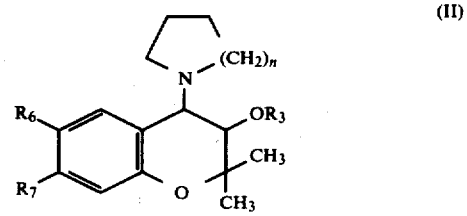

and salts and pro-drugs thereof wherein $R_3$, $R_6$ and $R_7$ have the values herein before indicated and n is 1 or 2, the cyclic amino and $OR_3$ moieties being trans.

Suitable and particularly favoured groups $R_6$ and $R_7$ are as hereinbefore described in relation to formula (I).

From the foregoing it will be realised that certain preferred compounds of this invention are those of the formulae (III) and (IV):

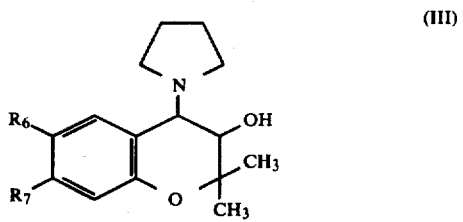

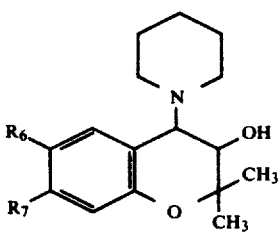

and salts thereof wherein $R_6$ and $R_7$ are as hereinbefore indicated, the cyclic amino and hydroxyl moieties being trans.

Suitable and particularly favoured groups $R_6$ and $R_7$ are as hereinbefore described in relation to formula (I).

Other classes of compounds of particular note are those of the formula (V):

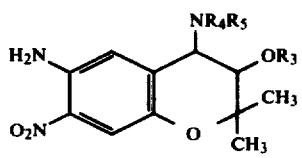

and salts and pro-drugs therefore wherein $R_3$, $R_4$ and $R_5$ are as hereinbefore indicated, the $NR_4R_5$ and $OR_3$ moieties are trans.

The compounds of the invention exist in optically active forms. Those skilled in the chemical arts will realise that racemic mixtures of amino compounds can be separated into pure optical isomers using such techniques as fractional crystallisation using optically active acids or the like.

The present invention also provides a process for the preparation of a compound of the formula (I) which comprises the reaction of a compound of the formula (VI):

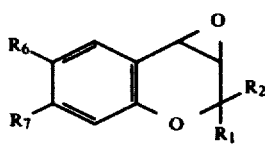

wherein $R_1$, $R_2$, $R_6$ and $R_7$ are as defined in relation to formula (I) with the proviso that any amino group present in $R_6$ or $R_7$ is masked; with a compound of the formula (VII):

Ti $HNR_4R_5$ (VII)

wherein $R_4$ and $R_5$ are as defined in relation to formula (I); and thereafter if desired or necessary converting $R_3$, $R_6$ or $R_7$ in the thus formed compound to another group $R_3$, $R_6$ or $R_7$, removing the "masking" from any amino group present in $R_6$ or $R_7$, or forming a salt of the compound.

The reaction with the epoxide may be carried out at any non-extreme low, medium or high temperature (for example, $-10°$ C. to $200°$ C.) but in general ambient or slightly elevated temperatures are most suitable (for example $12°$ C. to $100°$ C.). The reaction is normally carried out in a solvent such as an alcohol or ketone, for example methanol, ethanol, propanol, acetone or methylethylketone.

It has been found that the reaction proceeds smoothly if carried out in refluxing ethanol.

The above reaction gives a trans product substantially free of the cis-isomer.

The desired product may be obtained from the reaction mixture by removal of the solvent which is normally accomplished by evaporation under reduced pressure. The initial product may contain some epoxide. This may be separated by dissolving the reaction product in ethyl acetate and extracting into dilute acid. If desired the solvent may be evaporated at this stage but it is usually more convenient to neutralise, back extract into ethyl acetate and recover by evaporation at reduced pressure.

The groups $R_3$, $R_6$ and $R_7$ may be interconverted in the usual way. For example a $R_3$ hydrogen can be methylated, ethylated or propylated, and a $R_7$ cyano can be converted to a $R_7$ carboxamido by treatment with acid.

The term "masking" herein means reversibly protecting in a manner which temporarily renders the amino group non-basic. Suitable methods of masking include acylation. The acylamino group may be converted to the amino group by such conventional processes as hydrolysis after the addition reaction has been effected.

If it is desired to deprotect a protected amino group in the presence of a cyano group then a more suitable method is to use a trifluoroacetyl protecting group which may be removed by mild hydrolysis. A further suitable method of deprotection of a protected amino group in the presence of a cyano group is to utilise a benzyloxycarbonyl or p-nitrobenzyloxycarbonyl protecting group which groups may be removed by mild catalytic hydrogenolysis. Benzyloxycarbonyl amino and p-nitrobenzyloxycarbonylamino groups may be formed by reaction of the appropriate chloride with the free amine function.

If a salt is desired this may be prepared from the free base in the usual way, for example the free base may be dissolved in diethyl ether containing a little ethanol and treated with a solution of the acid for example in diethyl ether. The desired salt may then be collected by filtration.

Etherification of the initially produced compound of the formula (I) wherein $R_3$ is a hydrogen atom may be effected in conventional manner such as reaction with an alkyl iodide in the presence of a base such as potassium t-butoxide in an inert solvent such as toluene. If required, $R_6$ may be suitably protected during this etherification reaction and subsequently deprotected.

Preparation of esters of the compounds of formula (I) wherein $R_3$ is hydrogen may be by such conventional methods of esterification as reaction with an acylating agent optionally in the presence of an acid acceptor. Suitable acylating agents include acid halides such as bromides, chlorides and anhydrides.

Esters of the compound of the formula (I) wherein $R_3$ is hydrogen also may be prepared by reaction with an acid in the presence of a condensation promoting agent such as dicyclohexylcarbodiimide or its chemical equivalent. Such reactions are generally carried out in a non-hydroxylic solvent at a non-extreme temperature. If required, $R_6$ can be suitably masked during this acylation step and then deprotected.

The epoxides of the formula (VI) may be isolated or used in situ and may be prepared according to the following reaction sequence.

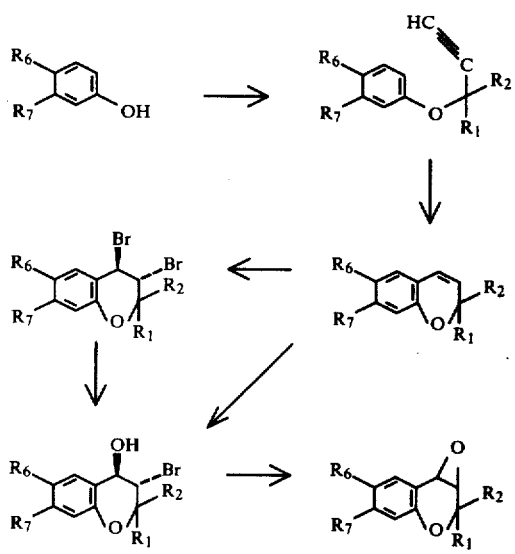

This reaction sequence may be brought about under conditions analogous to those described in the aforementioned U.K. Patents.

The above reaction sequence can produce mixtures of compounds owing to the two methods of ring closure of the propargyl ether. It is thus useful to separate any undesired isomer of the chromene before proceeding, for example chromatographically. Also a monofunctional chromene may be converted to a difunctional one by chemical manipulation in known manner, for example a nitro group may be introduced next to an acetamido group.

In a further aspect the product invention also provides a pharmaceutical composition which comprises a compound of this invention and a pharmaceutically acceptable carrier.

The compositions of this invention are most suitably adapted for oral administration although adaption for other modes of administration for example by injection are also possible.

In order to obtain consistency of administration it is preferred that the compositions of this invention are in the form of a unit dose. Suitable unit dose forms include tablets, capsules, ampoules and powders in sachets. Such unit dose forms aptly contain from 1 to 100 mg of the compound of this invention and more usually from 2 to 75 mg, for example 5 to 50 mg. Such compositions may be administered from 1 to 6 times a day, more usually from 2 to 4 times a day, in a manner such that the daily dose is from 5 to 200 mg for a 70 kg human adult and more aptly from 10 to 100 mg.

Shaped compositions are favoured composition aspects.

The compositions of this invention may be formulated in conventional manner, for example in a manner similar to that used for known antihypertensive agents such as hydrallazine.

In addition such compositions may contain further active agents such as other antihypertensive agents especially $\beta$-blocking agents, and diuretics.

The following Examples illustrate the invention.

EXAMPLE 1

(a) 6-Acetamido-3,4-dihydro-2,2-dimethyl-7-nitro-trans-4-pyrrolidino-2H-benzo[b]pyran-3-ol hydrochloride, (b) 6-Acetamido-3,4-dihydro-2,2-dimethyl-7-nitro-trans-4-piperidino-2H-benzo[b]pyran-3-ol and (c) 6-Acetamido-3,4-dihydro-2,2-dimethyl-trans-4-isopropylamino-7-nitro-2H-benzo[b]pyran-3-ol methanol sulphonates To 6-Acetamido-2,2-dimethyl-7-nitro-2H-benzo[b]pyran (10.78 g, the preparation of which was disclosed in British Pat. No. 1,548,222 dissolved in dimethyl sulphoxide (100 ml) containing water (1.48 ml) was added freshly recrystallised N-bromosuccinimide (14.59 g) with vigorous stirring. Dilution with water (700 ml) and filtration and drying of the solid obtained gave 6-Acetamido-trans-3-bromo-3,4-dihydro-2,2-dimethyl-7-nitro-2H-benzo[b]pyran-4-ol as a yellow solid (14.06 g). A small portion recrystallised from ethanol had m.p. 198°–200°; nmr (CDCl$_3$/DMSOd$_6$) $\delta$ 1.62 (3H), 1.79 (3H), 2.37 (3H), 4.27 (1 exchangeable H, m) overlapped with 4.35 (1H, d, J=9), 5.01 (1H, d, J=9), 7.83 (1H), 8.56 (1H), 10.02 (1 excangeable H, m). Anal. Calcd for C$_{13}$H$_{15}$N$_2$O$_5$Br: C, 43.47; H, 4.21; N, 7.80. Found: C, 43.70; H, 4.37; N, 7.46%.

This bromohydrin (14.02 g), sodium hydroxide pellets (14.00 g) dioxan (750 ml) and water (140 ml) were stirred at room temperature during 3 hours. Evapporation to half volume and addition of water (1 l) and extraction via ethyl acetate (3×500 ml), and washing of the combined organic layers with water and brine, drying and solvent removal gave a red gummy solid (11.12 g). Recrystallisation from ethanol gave 6-acetamido-3,4-dihydro-2,2-dimethyl-3,4-epoxy-7-nitro-2H-benzo[b]pyran as a yellow solid (5.92 g) of m.p. 156°–158°; nmr $\delta$ (CDCl$_3$) 1.27 (3H), 1.60 (3H), 2.25 (3H), 3.53 (1H, d, J=4), 3.98 (1H, d, J=4), 7.62 (1H), 8.77 (1H), 10.05 (1H). Manipulation of the mother liquors gave an additional crop of epoxide (0.74 g). Anal. Calcd for C$_{13}$H$_{14}$N$_2$O$_5$: C, 56.11; H, 5.07; N, 10.07. Found: C, 55.92; H, 5.27; N, 9.82%.

This epoxide (4.40 g) and piperidine (1.60 ml) were refluxed in ethanol (80 ml) for 16 hours. Removal of solvent, addition of ether, washing with water before drying, following by filtration gave the crude free base (3.54 g). Treatment of this crude material (0.70 g) in the minimum volume of ethanol with methane sulphonic acid (0.125 ml) followed by two recrystallisations from ethanol of the crude yellow solid obtained, gave 6-acetamido-3,4-dihydro-2,2-dimethyl-7-nitro-trans-4-piperidino-2H-benzo[b]pyran-3-ol methane sulphonate of m.p. 200°–204° C.; nmr (DMSOd$_6$) $\delta$ 1.09 (3H), 1.44 (3H), 1.63 (6H, broad m), 2.05 (3H), 2.43 (3H), 3.55 (6H, broad m, including 2 exchangeable H), 4.20 (1H, d, J=9), 4.67 (1H, d, J=9), 7.41 (1H), 7.98 (1H), 10.17 (1 exchangeable H). Anal. Calcd for C$_{19}$H$_{29}$N$_3$O$_8$S: C, 49.66; H, 6.36; N, 9.15; S, 7.00. Found: C, 49.75; H, 6.35; N, 8.97; S, 7.23%. Similarly prepared was 6-Acetamido-3,4-dihydro-2,2-dimethyl-trans-4-isopropyl-amino-7-nitro-2H-benzo[b]pyran-3-ol methane sulphonate m.p. 185°–189° as a pale yellow powder from n-propanol-diethyl ether; nmr (DMSOd$_6$) $\delta$ 1.13 (3H), 1.43 (9H, broad m), 2.49 (6H), 3.60–5.95 (indistinct series of m), 7.37 (2H), 8.75 (1H, broad m). Anal. Calcd for C$_{17}$H$_{27}$N$_3$O$_8$S: C, 47.10; H, 6.28; N, 9.70; S, 7.42. Found: C, 46.67; H, 6.33; N, 8.81; S, 7.45%. Substitution of pyrrolidine for piperidine in the reaction with the epoxide, followed by similar work up, and treatment of the crude free base in dry ether with ethereal hydrogen chloride gave 6-Acetamido-3,4-dihydro-2,2-dimethyl-7-nitro-trans-pyrrolidino-2H-benzo[b]pyran-3-ol hydrochloride as a dark red foam m.p. 138°–143°; nmr (DMSOd$_6$) δ 1.03 (3H), 1.41 (3H) 2.02 (7H, broad m), 3.31 (4H, broad m), 3.99 (1H, d, J=8), 4.67 (1H, d, J=8), 7.39 (1H), 7.70 (1H). Mass spectrum: initial cleavage of O-C$_2$ and C$_3$-C$_4$ bonds (retro Diels-Alder) gave a peak at m/e 277. Anal. Calcd for C$_{17}$H$_{24}$NO$_5$Cl: C, 52.91; H, 6.27; N, 10.89; Cl, 9.20. Found: C, 52.68; H, 6.46; N, 10.03; Cl, 9.62%.

EXAMPLE 2

(a) 6-Amino-3,4-dihydro-2,2-dimethyl-7-nitro-trans-4-pyrrolidino-2H-benzo[b]pyran-3-ol hydrochloride,
(b) 6-Amino-3,4-dihydro-2,2-dimethyl-7-nitro-trans-4-piperidino-2H-benzo[b]pyran-3-ol and
(c) 6-Amino-3,4-dihydro-2,2-dimethyl-trans-4-isopropylamino-7-nitro-2H-benzo[b]pyran-3-ol methane sulphonates The crude free base (2.84 g, obtained from the reaction of 6-acetamido-3,4-epoxy-3,4-dihydro-2,2-dimethyl-7-nitro-2H-benzo[b]pyran with piperidine in Example 1) and 5 N hydrochloric acid (45 ml) were refluxed in ethanol (80 ml) for 3 hours. Dilution with water, basification and extraction via ethyl acetate, followed by drying, evaporation, etc., gave the crude free base as a red foam (2.41 g). Treatment of this material in the minimum volume of ethanol-diethyl ether with methane sulphonic acid until precipitation had ceased and recrystallisation from ethanol-diethyl ether gave 6-amino-3,4-dihydro-2,2-dimethyl-7-nitro-trans-4-piperidino-2H-benzo[b]pyran-3-ol methane sulphonate as brick red crystals (2.47 g) of m.p. 243°–244° C.; nmr (DMSOd$_6$) δ 1.06 (3H), 1.47 (3H), 1.74 (6H, broad m), 2.49 (3H), 3.30 (4H, broad m), 3.88–4.94 (4H, broad m), overlapped with 4.20 (1H, d, J=8) and 4.59 (1H, d, J=8), 7.42 (1H), 7.62 (1H). Anal. Calcd for C$_{17}$H$_{27}$N$_3$O$_7$S: C, 48.92; H, 6.52; N, 10.07; S, 7.71. Found: C, 48.74; H, 6.62; N, 9.72; s, 7.52%.

Similarly prepared was 6-Amino-3,4-dihydro-2,2-dimethyl-trans-4-isopropyl-amino-7-nitro-2H-benzo[b]pyran-3-ol methane sulphonate m.p. 243°–245° from ethanol-n-propanol-diethyl ether. Nmr (DMSOd$_6$) δ 1.09 (3H), 1.42 (9H, broad m), 2.38 (3H), 3.05–4.54 (7H, series of m), 7.32 (1H), 7.40 (1H). Anal. Calcd for C$_{15}$H$_{25}$N$_3$O$_7$S: C, 46.02; H, 6.44; N, 10.74; S, 8.22. Found: C, 46.27; H, 6.52; N, 10.71; S, 7.94%. Similarly, the crude free base obtained by reaction of 6-acetamido-3,4-epoxy-3,4-dihydro,2-,2-dimethyl-7-nitro-2H-benzo[b]pyran with pyrrolidine as in Example 1 was subject to acid hydrolysis, and work up as described above. Treatment of the crude free base in diethyl ether with ethereal hydrogen chloride gave 6-amino-3,4-dihydro-2,2-dimethyl-7-nitro-trans-4-pyrrolidino-2H-benzo[b]pyran-3-ol hydrochloride as red crystals m.p. 241°–243° from ethanol; nmr (DMSOd$_6$) δ 1.02 (3H), 1.41 (3H), 2.45 (4H, broad m), 3.37 (4H, broad m), 3.86–5.68 (6H, broad m), overlapped with 4.04 (1H, d, J=8) and 4.73 (1H, d, J=8), 7.40 (1H), 7.67 (1H); mass spectrum: initial cleavage of O-C$_2$ and C$_3$-C$_4$ bonds (retro Diels-Alder) gives a peak at m/e 235 in the EI spectrum; [M+H-HCl]$^+$ at m/e 308 in the FD spectrum. Anal. Calcd for C$_{15}$H$_{22}$N$_3$O$_4$Cl: C, 52.45; H, 6.45; N, 12.21; Cl, 10.32. Found: C, 52.33; H, 6.34; N, 11.82; Cl, 10.00%.

EXAMPLE 3

Biological Data

Systolic blood pressures were recorded by a modification of the tail cuff method described by J. M. Claxton, M. G. Palfreyman, R. H. Poyser and R. L. Whiting, European Journal of Pharmacology, 37, 179 (1976). An oscilloscope of W+W BP recorder, model 8002, was used to display pulses. Prior to all measurements rats were placed in a heated environment (33.5°±0.5° C.) before transfer to a restraining cage. Each determination of blood pressure was the mean of at least 6 readings. Spontaneously hypertensive rats (aged 12–18 weeks) with systolic blood pressures >170 mmHg were considered hypertensive.

| Compound of Example No. | Time Post dose (hrs) | % change in Systolic Blood pressure | % change in heart rate |
|---|---|---|---|
| 1(a) | Initial value | 194 ± 3 | 464 ± 5 |
| at 3 mg/kg | 1 | −37* | +13* |
| p.o. | 2 | —* | —* |
| 6 rats | 4 | −26 ± 3 | +4 ± 8 |
|  | 6 | −16 ± 3 | −1 ± 4 |
|  | 24 | −2 ± 3 | +5 ± 7 |
| 1(b) | Initial value | 199 ± 5 | 474 ± 4 |
| at 1 mg/kg | 1 | −10 ± 3 | +2 ± 1 |
| p.o. | 2 | −13 ± 2 | −2 ± 1 |
| 6 rats | 4 | −13 ± 3 | −5 ± 3 |
|  | 6 | −22 ± 3 | −10 ± 2 |
|  | 24 | −10 ± 4 | −14 ± 3 |
| 2(a) | Initial value | 189 ± 4 | 387 ± 28 |
| at 1 mg/kg | 1 | −24 ± 1 | +24 ± 11 |
| p.o. | 2 | −26 ± 2 | +20 ± 10 |
| 6 rats | 4 | −37 ± 1 | +15 ± 8 |
|  | 6 | −29 ± 1 | +6 ± 5 |
|  | 24 |  |  |
| 2(b) | Initial value | 200 ± 1 | 460 ± 17 |
| at 1 mg/kg | 1 | −20 ± 0 | −7 ± 4 |
| p.o. | 2 | −30 ± 1 | −2 ± 4 |
| 6 rats | 4 | −34 ± 1 | −1 ± 3 |
|  | 6 | −30 ± 2 | −6 ± 6 |
|  | 24 | −11 ± 3 | −6 ± 2 |
| 2(c) | Initial value | 174 ± 3 | 402 ± 13 |
| at 30 mg/kg | 1 | −14 ± 5 | +5 ± 3 |
| p.o. | 2 | −16 ± 5 | +5 ± 2 |
| 6 rats | 4 | −9 ± 2 | +4 ± 5 |
|  | 6 | −11 ± 4 | +3 ± 5 |
|  | 24 | −4 ± 3 | −2 + 4 |

*At 1 hour only 1 animal had measurable pulse. At 2 hrs all animals had no measurable pulses.

Toxicity

No toxic effects were observed in these tests.
We claim:
1. A compound of the formula:

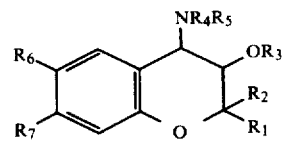

or a pharmaceutically acceptable salt or ester thereof, wherein R$_1$ is hydrogen or lower alkyl;
R$_2$ is hydrogen or lower alkyl;
R$_3$ is hydrogen or lower alkyl;
R$_4$ is hydrogen or lower alkyl;
R$_5$ is lower alkyl or alkyl of 3 to 5 carbon atoms terminally substituted by chlorine;

or R4 and R5 are joined so that together with the nitrogen atom to which they are attached they form a 6- or 7-membered saturated heterocyclic ring containing said nitrogen atom as the sole hetero atom or a 5-membered saturated heterocyclic ring optionally containing an oxygen or sulphur atom as an additional hetero atom;

R6 is amino, carboxylic acylamino of up to 3 carbon atoms, alkylamino of up to 3 carbon atoms, or dialkylamino of up to 3 carbon atoms in each alkyl moiety;

R7 is nitro or cyano; and the NR4R5 and OR3 groups are trans.

2. A compound according to claim 1 of the formula

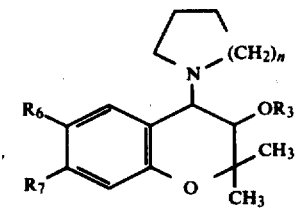

or a pharmaceutically acceptable salt or ester thereof wherein R3, R6 and R7 are as defined in claim 1 and n is 1 or 2, the cyclic amino and OR3 groups being trans.

3. A compound according to claim 2 of the formula:

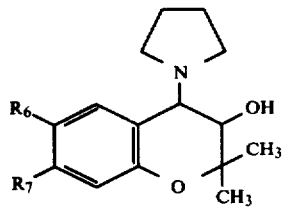

[(III)]

4. A compound according to claim 2 of the formula:

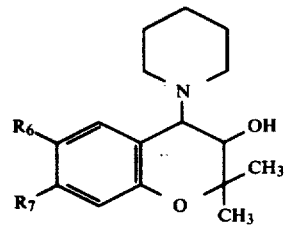

[(IV)]

5. A compound according to claim 1, wherein R4 and R5 are joined so that together with the nitrogen atom to which they are attached they form pyrrolidino or piperidino.

6. A compound according to claim 1 wherein R6 is amino or acetamido.

7. A compound according to claim 1 wherein R7 is nitro.

8. An anti-hypertensive composition comprising an anti-hypertensively effective amount of a compound according to claim 1 in combination with a pharmaceutically acceptable carrier.

9. A method of effecting an anti-hypertensive response in a human or other animal which comprises administering thereto an effective amount of a compound according to claim 1.

* * * * *